(12) United States Patent
Liang et al.

(10) Patent No.: US 10,377,702 B1
(45) Date of Patent: Aug. 13, 2019

(54) HYDROXYTYROSOL ISOPHORONE DIISOCYANNATE DERIVATIVE WITH ANTIOXIDANT ACTIVITY AND A METHOD OF PREPARING THE SAME

(71) Applicants: Chengyuan Liang, Xi'an (CN); Yuzhi Liu, Xi'an (CN); Xingke Ju, Xi'an (CN); Yonghong Tang, Xi'an (CN); Gennian Mao, Xi'an (CN); Qianqian Zhao, Xi'an (CN); Bin Tian, Xi'an (CN); Jian Zha, Xi'an (CN); Chunyang Shi, Xi'an (CN); Yongbo Wang, Xi'an (CN); Huayin Pu, Xi'an (CN); Yanghan Liu, Xi'an (CN)

(72) Inventors: Chengyuan Liang, Xi'an (CN); Yuzhi Liu, Xi'an (CN); Xingke Ju, Xi'an (CN); Yonghong Tang, Xi'an (CN); Gennian Mao, Xi'an (CN); Qianqian Zhao, Xi'an (CN); Bin Tian, Xi'an (CN); Jian Zha, Xi'an (CN); Chunyang Shi, Xi'an (CN); Yongbo Wang, Xi'an (CN); Huayin Pu, Xi'an (CN); Yanghan Liu, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 16/426,560

(22) Filed: May 30, 2019

(51) Int. Cl.
  *C07C 269/02* (2006.01)
  *B01J 31/02* (2006.01)
  *B01D 15/16* (2006.01)

(52) U.S. Cl.
  CPC ......... *C07C 269/02* (2013.01); *B01D 15/165* (2013.01); *B01J 31/0237* (2013.01)

(58) Field of Classification Search
  CPC ... C07C 269/02; C07C 269/04; B01D 15/165; B01J 31/0237
  See application file for complete search history.

(56) References Cited

U.S. PATENT DOCUMENTS

2016/0060405 A1*  3/2016  Kuwayama ............... C08J 5/18
                                                      428/1.33

FOREIGN PATENT DOCUMENTS

DE           3800295      *  7/1989

* cited by examiner

*Primary Examiner* — Jafar F Parsa

(57) ABSTRACT

A compound having the formula (I):

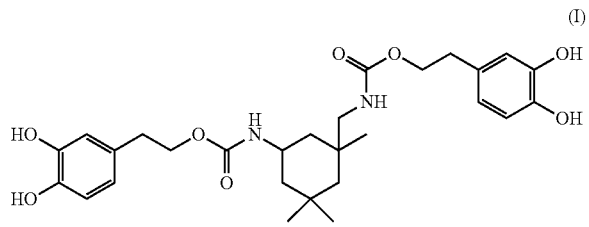

is disclosed. A method of preparing the compound of formula (I) is also disclosed.

10 Claims, 1 Drawing Sheet

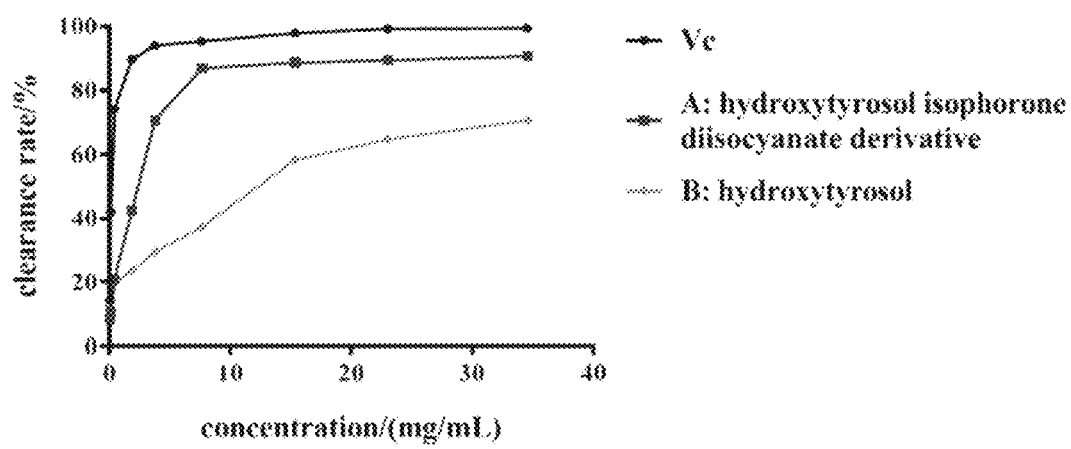

HYDROXYTYROSOL ISOPHORONE DIISOCYANNATE DERIVATIVE WITH ANTIOXIDANT ACTIVITY AND A METHOD OF PREPARING THE SAME

FIELD OF THE INVENTION

The present invention relates to food chemistry area, more specifically, a hydroxytyrosol isophorone diisocyanate derivative, its preparation method and application.

Oil and fat play an important role in people's daily life, which can provide energy to the human body and have important physiological functions in the human body. Oxidation of fats and oils refers to the oxidation reaction of foods on the surface and inside of foods under the action of light, radiation, air and enzymes. The products of oil oxidation not only affect the flavor and color of oils and fats, but also reduce the quality of foods. Oxidation of oils and fats can cause damage to membranes, enzymes and proteins, leading to many diseases of aging and even carcinogenicity, which seriously endangers human health. In order to extend the shelf life of oil and fact, adding antioxidants to oil and fat is one of the most effective means. However, several commonly used synthetic antioxidants have certain safety hazards, which are strongly opposed or restricted in some countries. Therefore, research on antioxidants has gradually turned to the application of natural antioxidants.

Hydroxytyrosol (compound of Formula (II)) that can be extracted from olive oil is a natural polyphenolic compound with a variety of biological and pharmacological activities. It plays a role in the prevention and treatment of cancer, inflammatory, cardiovascular and cerebrovascular diseases, and coronary heart disease and the protection of retinal pigment epithelial cells. The molecular structure of hydroxytyrosol has not only a phenolic hydroxyl group like other phenolic substances, but also an alcoholic hydroxyl group in an ethanol chain to which a benzene ring is attached. Therefore, hydroxytyrosol has excellent antioxidant activity. It is inferred that the antioxidant activity of hydroxytyrosol is closely related to its structure: hydroxytyrosol has an alcoholic hydroxyl group as a hydrogen donor, which has a destructive effect on various active oxygen species, and can reduce singlet oxygen 02 to a less active triplet oxygen 02, reducing the possibility of oxygen free radical generation; on the other hand, hydroxytyrosol is an effective scavenger for various free radicals, which reacts to produce less reactive polyphenolic radicals, interrupting the chain reaction of free radical oxidation; finally, the ortho-diphenolic hydroxyl group of hydroxytyrosol can be combined with metal ions to reduce the catalysis of metal ions to the oxidation reaction.

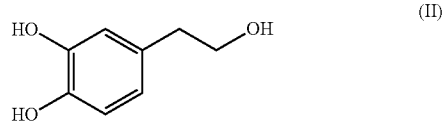 [SMILES: OCCc1ccc(O)c(O)c1]

(II)

Isophorone diisocyanate (IPDI) (compound of Formula (III)) is an excellent aliphatic diisocyanate which is a nonyellowing aliphatic isocyanate. It is a colorless or pale yellow liquid at normal temperature and has a lower activity than aromatic isocyanate. Polyurethane adhesive made of isophorone diisocyanate has excellent optical stability and chemical resistance, and is widely used in plastics, adhesives, medicines and perfumes. It is a promising high-performance material.

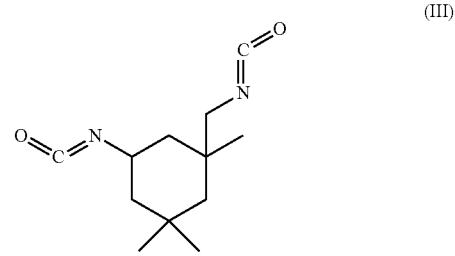 [SMILES: CC1(C)CC(N=C=O)CC(C)(CN=C=O)C1]

(III)

In the present invention, isophorone diisocyanate is modified by the hydroxytyrosol structure to obtain a hydroxytyrosol isophorone diisocyanate derivative. Preliminary antioxidant experiment shows that the compound has excellent antioxidant activity and has high medical research and application value in the field of antioxidant food, medicine and health products.

SUMMARY OF THE INVENTION

In one embodiment, the present invention provides a hydroxytyrosol isophorone diisocyanate derivative which can be used as an anti-oxidation and preparation of scavenging free radical product in the fields of food, health care products and medicine. The hydroxytyrosol isophorone diisocyanate derivative has the following Formula (I):

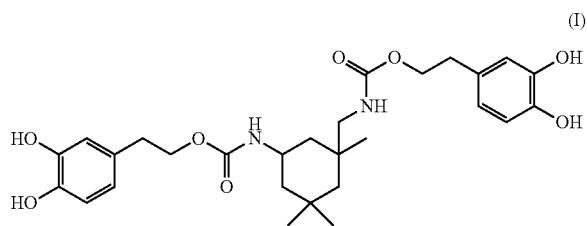 [SMILES: CC1(C)CC(NC(=O)OCCc2ccc(O)c(O)c2)CC(C)(CNC(=O)OCCc2ccc(O)c(O)c2)C1]

(I)

In another embodiment, the present invention provides a method of preparing the compound of formula (I). The method includes reacting a compound of formula (II) with a compound of formula (III) to obtain the compound of formula (I):

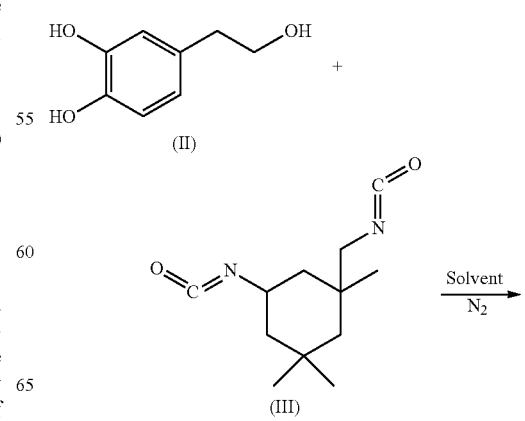

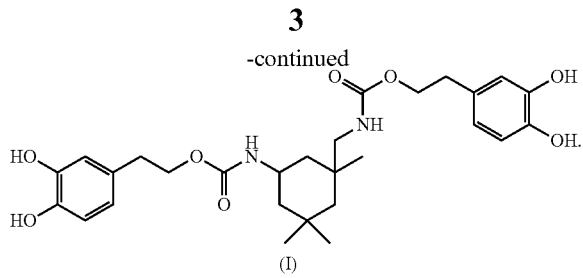

(I)

In another embodiment, the reaction of the compound of formula (II) with the compound of formula (III) includes the following steps: placing the compound of formula (II) and the compound of formula (III), in a molar ratio of 2.4:1 to 2.6:1, in a reactor; adding a solvent and a catalyst under nitrogen atmosphere to obtain a reaction mixture; heating the reaction mixture at 50-75° C. for 1-4 hours under magnetic stirring; concentrating the reaction mixture under reduced pressure to give a crude product; and purifying the crude product by flash chromatograph.

In another embodiment, the solvent is toluene, ethyl acetate or acetonitrile.

In another embodiment, the solvent is toluene.

In another embodiment, the molar ratio of the compound of formula (II) and the compound of formula (III) is 2.6:1.

In another embodiment, the catalyst is triethylamine or 4-dimethylaminopyridine.

In another embodiment, the catalyst is triethylamine.

In another embodiment, the reaction mixture is heated at 75° C.

In another embodiment, the reaction mixture is heated for 4 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 shows the scavenging activity of the sample and control solutions at different concentrations.

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

Example 1

Preparation of a Hydroxytyrosol Isophorone Diisocyanate Derivative: 3,4-dihydroxyphenethyl ((5-(((3,4-dihydroxyphenethoxy)-carbonyl)amino)-1,3,3-trimethylcyclohexyl)methyl)carbamate In a 100 mL three-necked flask, 87.9 mg (0.57 mmol) of hydroxytyrosol and 31 µL (0.22 mmol) of triethylamine were dissolved in 50 mL of toluene under nitrogen atmosphere. 50 mg (0.22 mmol) of isophorone diisocyanate was slowly added dropwise to the reaction solution. After isophorone diisocyanate was added, the temperature was raised to 75° C., and the reaction was carried out for 4 hours. Thin layer chromatography was used to monitor the reaction to completion, heating was stopped, and the protective device was removed. The reaction mixture was concentrated under reduced pressure to give a crude product. The crude product was purified by silica gel column chromatography, ethyl acetate:petroleum ether=3:10 as eluent, and the eluent was concentrated under reduced pressure and dried to obtain 79.7 mg of the titled compound, a yield of 68.32%.

3,4-dihydroxyphenethyl ((5-(((3,4-dihydroxyphenethoxy)-carbonyl)amino)-1,3,3-trimethylcyclohexyl)methyl)carbamate: $^1$H-NMR (400 MHz, DMSO-$d_6$) δ (ppm): 8.46 (2H, b), 6.90 (2H, s), 6.83~6.71 (4H, m), 5.57 (4H, s), 4.62 (4H, t), 3.75 (H, m), 2.99~2.81 (6H, m), 1.84~1.67 (4H, m), 1.63~1.12 (5H, m), 1.01 (6H, s); $^{13}$C-NMR (400 MHz, DMSO-$d_6$) δ (ppm): 159.3, 157.2, 148.6, 146.2, 130.5, 125.8, 117.4, 116.9, 64.6, 49.6, 47.5, 43.8, 33.6, 28.1, 24.5, 20.1; MS (ESI) for (M+H)$^+$: 531.3.

Example 2

Preparation of 3,4-dihydroxyphenethyl ((5-(((3,4 dihydroxyphenethoxy)-carbonyl)amino)-1,3,3-trimethylcyclohexyl)methyl)carbamate In a 100 mL three-necked flask, 87.9 mg (0.57 mmol) of hydroxytyrosol and 31 µL (0.22 mmol) of triethylamine were dissolved in 50 mL of ethylacetate under nitrogen atmosphere. 50 mg (0.22 mmol) of isophorone diisocyanate was slowly added dropwise to the reaction solution. After isophorone diisocyanate was added, the temperature was raised to 50° C., and the reaction was carried out for 2 hours. Thin layer chromatography was used to monitor the reaction to completion, heating was stopped, and the protective device was removed. The reaction mixture was concentrated under reduced pressure to give a crude product. The crude product was purified by silica gel column chromatography, ethyl acetate:petroleum ether=3:10 as eluent, and the eluent was concentrated under reduced pressure and dried to obtain 54.9 mg of the titled compound, a yield of 47.02%.

Example 3

Preparation of 3,4-dihydroxyphenethyl ((5-(((3,4 dihydroxyphenethoxy)-carbonyl)amino)-1,3,3-trimethylcyclohexyl)methyl)carbamate In a 100 mL three-necked flask, 81.7 mg (0.53 mmol) of hydroxytyrosol and 31 µL (0.22 mmol) of triethylamine were dissolved in 50 mL of acetonitrile under nitrogen atmosphere. 50 mg (0.22 mmol) of isophorone diisocyanate was slowly added dropwise to the reaction solution. After isophorone diisocyanate was added, the temperature was raised to 60° C., and the reaction was carried out for 4 hours. Thin layer chromatography was used to monitor the reaction to completion, heating was stopped, and the protective device was removed. The reaction mixture was concentrated under reduced pressure to give a crude product. The crude product was purified by silica gel column chromatography, ethyl acetate:petroleum ether=3:10 as eluent, and the eluent was concentrated under reduced pressure and dried to obtain 62.8 mg of the titled compound, a yield of 53.78%.

Example 4

Preparation of 3,4-dihydroxyphenethyl ((5-(((3,4 dihydroxyphenethoxy)-carbonyl)amino)-1,3,3-trimethylcyclohexyl)methyl)carbamate In a 100 mL three-necked flask, 87.9 mg (0.57 mmol) of hydroxytyrosol and 2.5 mg (0.02 mmol) DMAP (4-dimethylaminopyridine) were dissolved in 50 mL of toluene under nitrogen atmosphere. 50 mg (0.22 mmol) of isophorone diisocyanate was slowly added dropwise to the reaction solution. After isophorone diisocyanate was added, the temperature was raised to 60° C., and the reaction was carried out for 1 hour. Thin layer chromatography was used to monitor the reaction to completion, heating was stopped, and the protective device was removed. The reaction mixture was concentrated under reduced pressure to give a crude product. The crude product was purified by silica gel column chromatography, ethyl acetate:petroleum ether=3:10 as eluent, and the eluent was concentrated under reduced pressure and dried to obtain 30.0 mg of the titled compound, a yield of 25.69%.

Example 5

Preparation of 3,4-dihydroxyphenethyl ((5-(((3,4 dihydroxyphenethoxy)-carbonyl)amino)-1,3,3-trimethylcyclohexyl)methyl)carbamate In a 100 mL three-necked flask, 87.9 mg (0.57 mmol) of hydroxytyrosol and 2.5 mg (0.02 mmol) of DMAP were dissolved in 50 mL of ethyl acetate under nitrogen atmosphere. 50 mg (0.22 mmol) of isophorone diisocyanate was slowly added dropwise to the reaction solution. After isophorone diisocyanate was added, the temperature was raised to 75° C., and the reaction was carried out for 2 hours. Thin layer chromatography was used to monitor the reaction to completion, heating was stopped, and the protective device was removed. The reaction mixture was concentrated under reduced pressure to give a crude product. The crude product was purified by silica gel column chromatography, ethyl acetate:petroleum ether=3:10 as eluent, and the eluent was concentrated under reduced pressure and dried to obtain 65.5 mg of the titled compound, a yield of 56.15%.

Example 6

Preparation of 3,4-dihydroxyphenethyl ((5-(((3,4 dihydroxyphenethoxy)-carbonyl)amino)-1,3,3-trimethylcyclohexyl)methyl)carbamate In a 100 mL three-necked flask, 87.9 mg (0.57 mmol) of hydroxytyrosol and 31 μL (0.22 mmol) of triethylamine were dissolved in 50 mL of toluene under nitrogen atmosphere. 50 mg (0.22 mmol) of isophorone diisocyanate was slowly added dropwise to the reaction solution. After isophorone diisocyanate was added, the temperature was raised to 50° C., and the reaction was carried out for 1 hour. Thin layer chromatography was used to monitor the reaction to completion, heating was stopped, and the protective device was removed. The reaction mixture was concentrated under reduced pressure to give a crude product. The crude product was purified by silica gel column chromatography, ethyl acetate:petroleum ether=3:10 as eluent, and the eluent was concentrated under reduced pressure and dried to obtain 39.5 mg of the titled compound, a yield of 33.84%.

Example 7

The Antioxidant Activity of the Hydroxytyrosol Isophorone Diisocyanate Derivative Measured by a DPPH Radical Scavenging Activity Assay 2,2-Diphenyl-1-picryl hydrazyl (DPPH) is an organic compound composed of a stable organic radical. In the DPPH molecule, due to the presence of multiple electron-withdrawing —$NO_2$ and large π bonds of the benzene ring, nitrogen free radical is stabilized. Its methanol solution is purple and has a maximum absorption peak at 517 nm. After the addition of an antioxidant, DPPH captures an electron to be paired with the free electron, and the purple fades and turns into a yellow substance. The absorption at 517 nm disappears, and the degree of fading is quantitatively related to the number of electrons it captures. Based on this principle, a spectrophotometer is used to detect the change of the absorbance of the DPPH radical and the sample solution, and the ability of the sample to provide hydrogen atoms and scavenge free radicals can be measured.

Preparation of DPPH solution: measuring exact amount of 2,2-diphenyl-1-picryl hydrazyl (DPPH) and dissolving in toluene to prepare a 0.2 mmoL/L DPPH solution, stored at 0° C. in dark.

Preparation of test solution: Vc (vitamin C, positive control), hydroxytyrosol isophorone diisocyanate derivative (sample) and hydroxytyrosol (control). The sample solution was subjected to gradient dilution with toluene, and two sets of controls were separately dissolved in a test tube with a certain amount of toluene to prepare the same concentration gradient as the sample. The corresponding two groups of control solutions were obtained (gradient settings are shown in Table 1).

TABLE 1

Dilution gradient of the test solution

| Number | Test solution | Concentration gradient/(mg/mL) |
|---|---|---|
| Vc | Vc | 0.06, 0.12, 0.48, 1.92, 3.84, 7.68, 15.36, 23.04, 34.56 |
| A | Hydroxytyrosol isophorone diisocyanate derivative | 0.06, 0.12, 0.48, 1.92, 3.84, 7.68, 15.36, 23.04, 34.56 |
| B | Hydroxytyrosol | 0.06, 0.12, 0.48, 1.92, 3.84, 7.68, 15.36, 23.04, 34.56 |

Specific Steps:

Sample liquid absorbance measurement: Take 2 mL of sample solution (Table 1: Vc and B), add 2 mL of DPPH solution with concentration of $2*10^{-4}$ mol/L, mix and react in the dark at room temperature for 30 min, adjust to zero with toluene, and measure at 517 nm. The absorbance $A_i$ was simultaneously measured for the absorbance $A_j$ of 2 mL of toluene mixed with 2 mL of the sample solution and the absorbance $A_0$ of 2 mL of DPPH solution mixed with 2 mL of toluene (The experimental results are shown in Table 2).

TABLE 2

Absorbance test results of each test solution

| Sample | Absorbance | Concentration/(mg/mL) | | | | | | | | |
|---|---|---|---|---|---|---|---|---|---|---|
| | | 0.06 | 0.12 | 0.48 | 1.92 | 3.84 | 7.68 | 15.36 | 23.04 | 34.56 |
| Vc | $A_i$ | 0.814 | 0.549 | 0.246 | 0.100 | 0.060 | 0.050 | 0.025 | 0.014 | 0.012 |
| | $A_j$ | 0.005 | 0.003 | 0.002 | 0.002 | 0.003 | 0.006 | 0.005 | 0.007 | 0.006 |
| | $A_0$ | | | | | 0.944 | | | | |
| A | $A_i$ | 0.975 | 0.953 | 0.843 | 0.615 | 0.319 | 0.155 | 0.128 | 0.122 | 0.110 |
| | $A_j$ | 0.003 | 0.006 | 0.005 | 0.005 | 0.008 | 0.015 | 0.007 | 0.009 | 0.010 |
| | $A_0$ | | | | | 1.062 | | | | |
| B | $A_i$ | 0.990 | 0.989 | 0.903 | 0.868 | 0.807 | 0.730 | 0.492 | 0.425 | 0.351 |
| | $A_j$ | 0.020 | 0.031 | 0.015 | 0.022 | 0.026 | 0.037 | 0.030 | 0.034 | 0.025 |
| | $A_0$ | | | | | 1.108 | | | | |

Clearance calculation: clearance rate (%) $[1-(A_i-A_j)/A_0]*100\%$

TABLE 3

DPPH clearance rate experiment results

| Concentration/ | Clearance rate/% (n = 3) | | |
|---|---|---|---|
| (mg/mL) | Vc | A | B |
| 0.06 | 14.35% | 8.45% | 12.44% |
| 0.12 | 42.15% | 10.80% | 13.52% |
| 0.48 | 74.20% | 21.06% | 19.87% |
| 1.92 | 89.63% | 42.53% | 23.64% |
| 3.84 | 94.01% | 70.69% | 29.55% |
| 7.68 | 95.32% | 86.84% | 37.41% |
| 15.36 | 97.88% | 88.59% | 58.30% |
| 23.04 | 99.22% | 89.36% | 64.72% |
| 34.56 | 99.39% | 90.62% | 70.59% |

The experimental results are shown in FIG. 1 and Tables 1 to 3. The antioxidant activity of the hydroxytyrosol isophorone diisocyanate derivative (A) showed a concentration-dependent relationship. As the concentration increases, the ability of the compound A to scavenge DPPH radicals is enhanced. In the concentration range, the DPPH free radical scavenging rate can reach up to 90.62%, and its antioxidant activity is basically the same as that of the positive control group (34.56 mg/mL) with positive antioxidant activity. Compared with the control group in which hydroxytyrosol (B) was added alone, the hydroxytyrosol isophorone diisocyanate derivative (A) at the same concentration was mostly superior in scavenging DPPH radicals. At a higher concentration, the antioxidant activity of the hydroxytyrosol isophorone diisocyanate derivative (A) was much higher than the equivalent concentration of the control group to which hydroxytyrosol (B) was added.

What is claimed is:

1. A compound having the following formula (I):

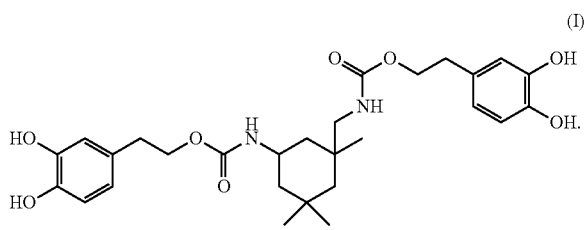 [SMILES: CC1(C)CC(NC(=O)OCCc2ccc(O)c(O)c2)CC(C)(CNC(=O)OCCc2ccc(O)c(O)c2)C1]

(I)

2. A method of preparing the compound of claim 1, comprising:
reacting a compound of formula (II) with a compound of formula (III) to obtain the compound of formula (I):

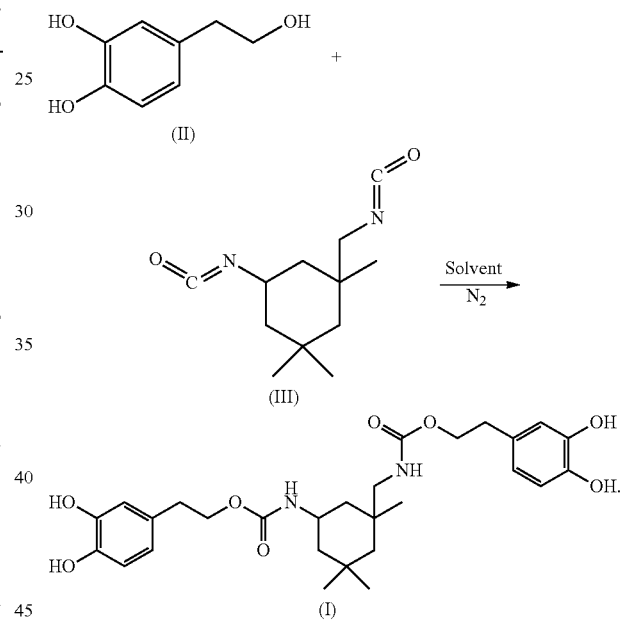

3. The method of claim 2, the reaction of the compound of formula (II) with the compound of formula (III) comprises the following steps:
placing the compound of formula (II) and the compound of formula (III), in a molar ratio of 2.4:1 to 2.6:1, in a reactor;
adding a solvent and a catalyst under nitrogen atmosphere to obtain a reaction mixture;
heating the reaction mixture at 50-75° C. for 1-4 hours under magnetic stirring;
concentrating the reaction mixture under reduced pressure to give a crude product; and
purifying the crude product by flash chromatograph.

4. The method of claim 3, wherein the solvent is toluene, ethyl acetate or acetonitrile.

5. The method of claim 4, wherein the solvent is toluene.

6. The method of claim 3, wherein the molar ratio of the compound of formula (II) and the compound of formula (III) is 2.6:1.

7. The method of claim 3, wherein the catalyst is triethylamine or 4-dimethylaminopyridine.

8. The method of claim 7, wherein the catalyst is triethylamine.

9. The method of claim 3, wherein the reaction mixture is heated at 75° C.

10. The method of claim 3, wherein the reaction mixture is heated for 4 hours.

\* \* \* \* \*